United States Patent [19]

Atkinson et al.

[11] Patent Number: 5,533,708
[45] Date of Patent: Jul. 9, 1996

[54] MEDICAL COUPLING SITE VALVE BODY

[75] Inventors: Gordon E. Atkinson, Cedarville; Thomas J. Solomon, Centerville, both of Ohio

[73] Assignee: Vernay Laboratories, Inc., Yellow Springs, Ohio

[21] Appl. No.: 378,506

[22] Filed: Jan. 26, 1995

Related U.S. Application Data

[63] Continuation-in-part of Ser. No. 153,998, Nov. 18, 1993, abandoned, which is a continuation-in-part of Ser. No. 44,830, Apr. 12, 1993, Pat. No. 5,295,657, which is a division of Ser. No. 893,813, Jun. 4, 1992, Pat. No. 5,251,873.

[51] Int. Cl.⁶ .................................................. F16L 37/28
[52] U.S. Cl. ...................... 251/149.1; 604/256; 604/905
[58] Field of Search .................... 251/149.1; 604/256, 604/905

[56] References Cited

U.S. PATENT DOCUMENTS

| | | | |
|---|---|---|---|
| 2,881,937 | 4/1959 | Roberts | 215/76 |
| 3,837,381 | 9/1974 | Arroyo | 251/149.1 |
| 4,143,853 | 5/1979 | Abramson | 251/149.1 |
| 4,387,879 | 6/1983 | Tauschinski | 251/149.1 |
| 4,436,519 | 3/1984 | O'Neill | 604/256 |
| 4,511,359 | 4/1985 | Vaillancourt | 604/411 |
| 4,568,336 | 2/1986 | Cooper | 604/240 |
| 4,607,671 | 8/1986 | Aalto et al. | 141/329 |
| 4,610,674 | 9/1986 | Suzuki et al. | 604/282 |
| 4,629,450 | 12/1986 | Suzuki et al. | 604/164 |
| 4,673,394 | 6/1987 | Fenton, Jr. et al. | 604/175 |
| 4,673,400 | 6/1987 | Martin | 604/905 |
| 4,683,916 | 8/1987 | Raines | 137/854 |
| 4,759,756 | 7/1988 | Forman et al. | 604/413 |
| 4,765,588 | 8/1988 | Atkinson | 251/149 |
| 4,786,281 | 11/1988 | Valentini et al. | 604/905 |
| 4,850,975 | 7/1989 | Furukawa | 604/170 |
| 4,874,377 | 10/1989 | Newgard et al. | 604/167 |
| 4,895,346 | 1/1990 | Steigerwald | 251/149.1 |
| 5,010,925 | 4/1991 | Atkinson et al. | 137/847 |
| 5,069,424 | 12/1991 | Dennany, Jr. et al. | 251/149.1 |
| 5,092,840 | 3/1992 | Healy | 604/83 |
| 5,100,394 | 3/1992 | Dudar et al. | 604/283 |
| 5,104,379 | 4/1992 | Nakamura et al. | 604/256 |
| 5,114,408 | 5/1992 | Fleischhaker et al. | 604/905 |
| 5,171,234 | 12/1992 | Jepson et al. | 604/283 |
| 5,190,067 | 3/1993 | Paradis et al. | 137/1 |
| 5,203,775 | 4/1993 | Frank et al. | 604/256 |
| 5,251,873 | 10/1993 | Atkinson | 251/149.1 |
| 5,280,876 | 1/1994 | Atkins | 251/149.1 |

FOREIGN PATENT DOCUMENTS

| | | |
|---|---|---|
| 86308392 | 5/1987 | European Pat. Off. . |
| 0314602 | 10/1988 | European Pat. Off. . |
| 3303718 | 10/1984 | Germany . |
| 8425197 | 10/1985 | Germany . |
| 3809127 | 4/1989 | Germany . |
| 3913392 | 10/1990 | Germany . |
| WO88/01881 | 3/1988 | WIPO . |
| WO90/11103 | 10/1990 | WIPO . |
| WO92/04936 | 4/1992 | WIPO . |
| WO92/19293 | 11/1992 | WIPO . |

Primary Examiner—A. Michael Chambers
Attorney, Agent, or Firm—Biebel & French

[57] ABSTRACT

The present invention provides a medical coupling site which is adapted to be attached directly to a standard male luer lock fitting. The coupling site includes a valve element contained within a tubular housing. The housing is provided with a threaded portion for engaging the threaded locking collar of a male luer lock whereby the male luer lock will be held in positive mechanical locking engagement with the coupling site. The valve element is provided with rib members extending inwardly from an inner wall of the valve element toward a slit formed in a diaphragm such that the rib members act to bias the slit to a closed position. The housing includes a flange extending radially inwardly over the diaphragm and defining a diameter for frictionally engaging a male luer in locking engagement. In addition, an exposed surface of the diaphragm is formed with surface texturing to define a roughened surface. The roughened surface reduces the surface friction between the diaphragm and a male luer as the luer is inserted through the diaphragm.

34 Claims, 13 Drawing Sheets

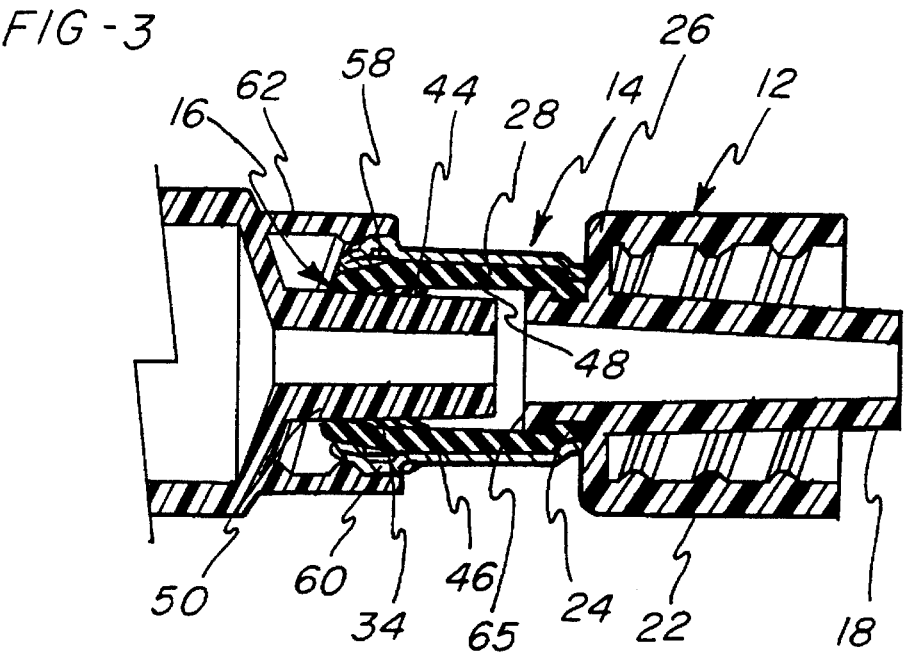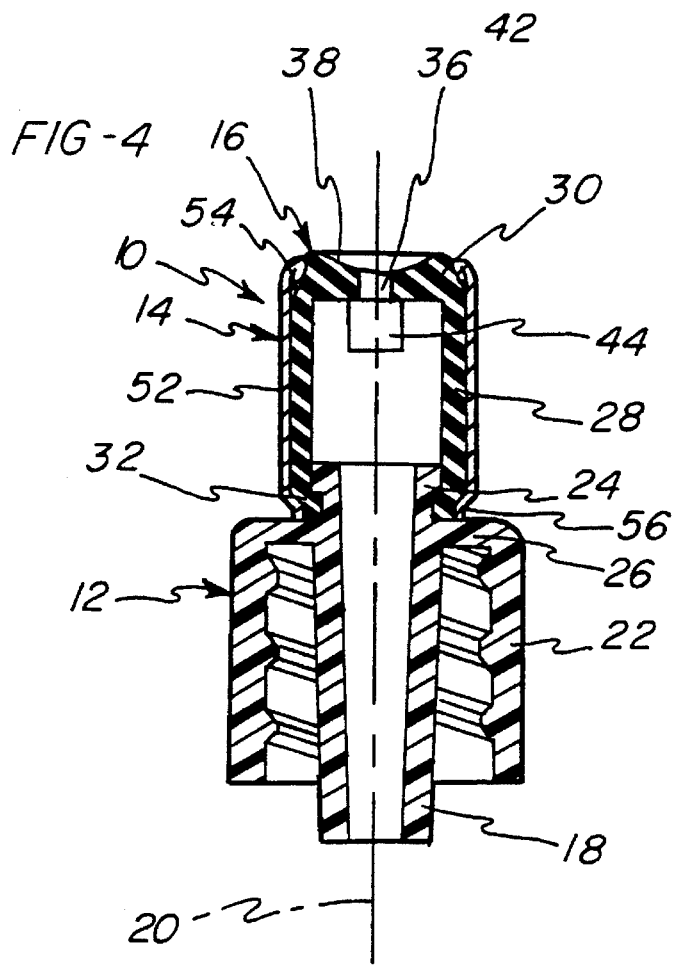

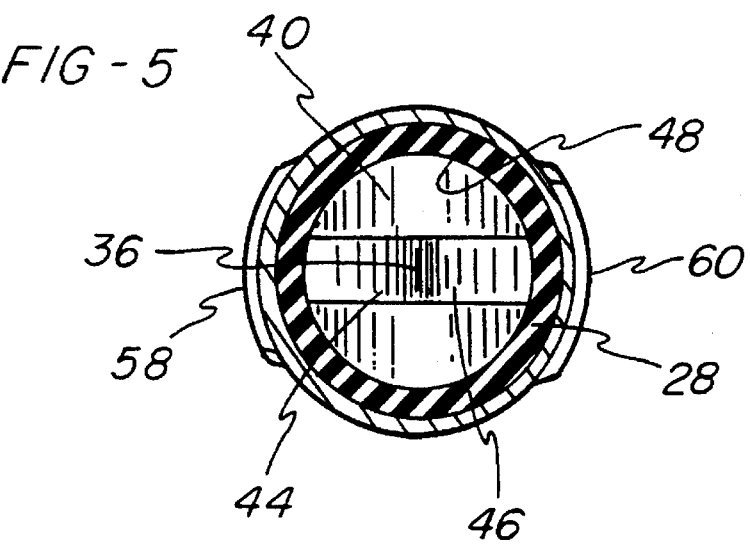
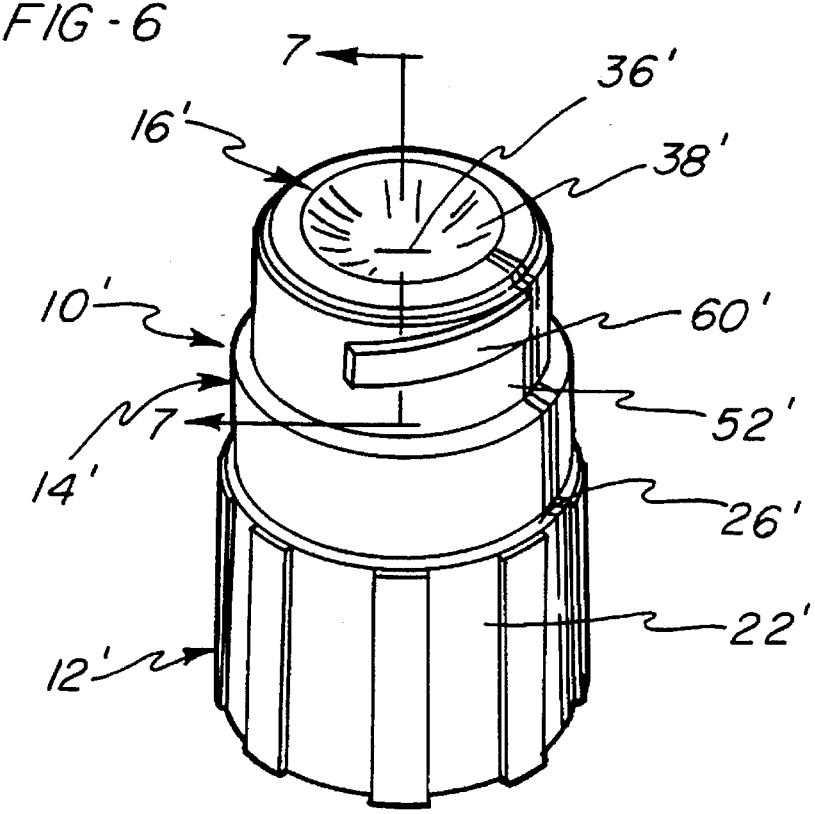

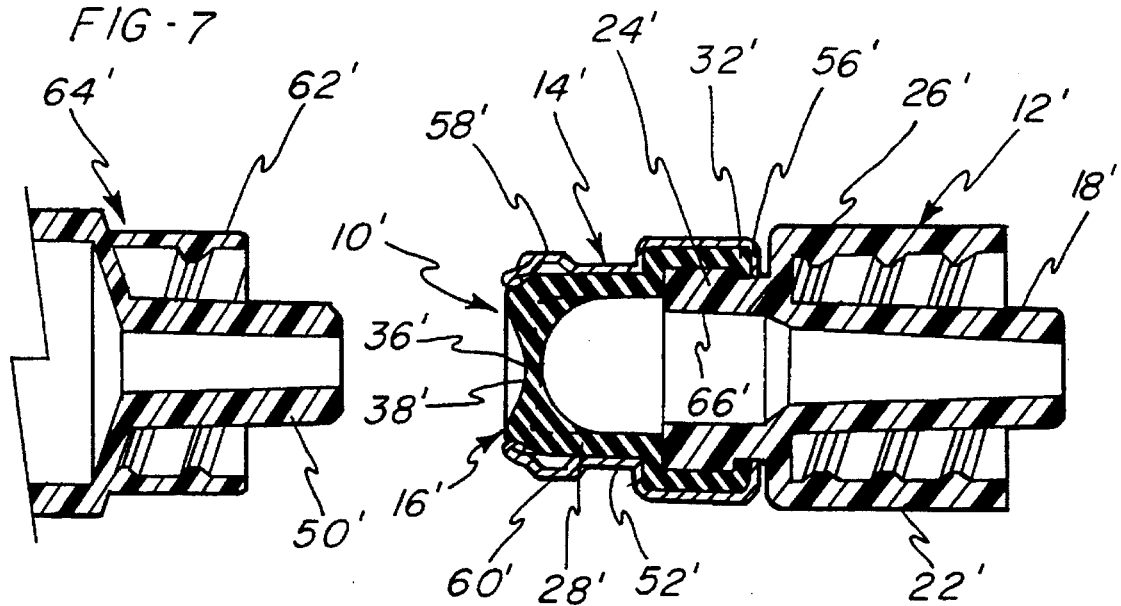
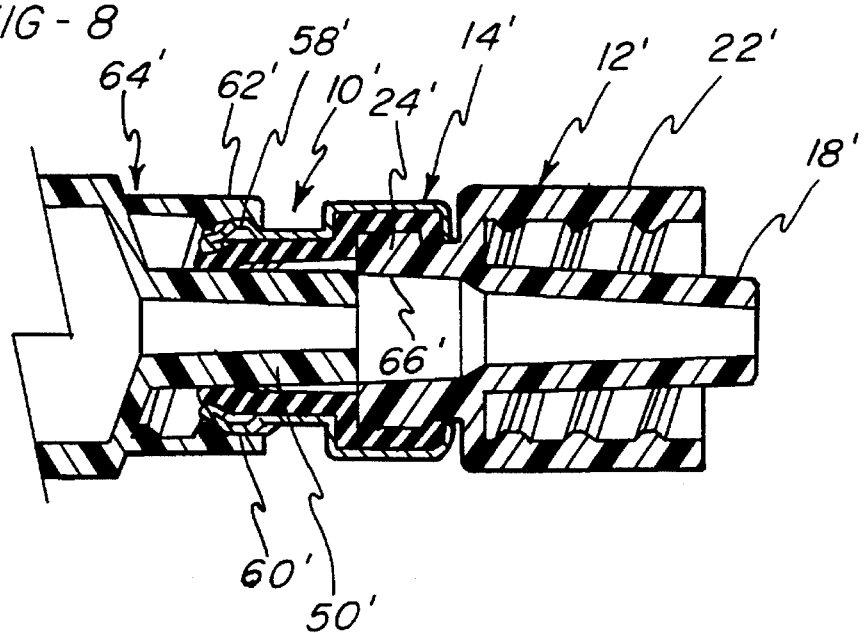

MEDICAL COUPLING SITE VALVE BODY

CROSS-REFERENCE TO RELATED APPLICATIONS

This application is a continuation-in-part of U.S. application Ser. No. 08/153,998, filed Nov. 18, 1993, now abandoned which is a continuation-in-part of U.S. application Ser. No. 08/044,830, filed Apr. 12, 1993, now U.S. Pat. No. 5,295,657 issued Mar. 22, 1994, which is a divisional of U.S. application Ser. No. 07/893,813, filed Jun. 4, 1992, now U.S. Pat. No. 5,251,873 issued Oct. 12, 1993, all assigned to the same assignee as this application.

BACKGROUND OF THE INVENTION

The present invention relates to a coupling site for use in medical applications and more particularly, to a coupling site which includes a valve element and support structure for cooperation with a standard male luer lock having a male luer taper and a threaded locking collar.

In recent years there has been increased concern with the spread of infectious diseases which may result from puncture wounds made by medical needles. There is also concern with the inconvenience of handling devices having needles which may inflict painful puncture wounds and which may be easily broken. However, needles have continued to be used in association with injection sites or other coupling sites in medical applications to transfer fluids to and from syringes or fluid conveying cannula. The continued use of needles for such coupling sites may be attributed to the convenience with which a needle may be inserted through a soft diaphragm wherein a fluid-tight seal is formed around the needle and, subsequently the needle may be withdrawn from the diaphragm resulting in the diaphragm resiliently filling in and closing the aperture formed by the needle. Thus, needle type injection sites have the advantages of providing quick access for a fluid cannula as well as providing an access site which ensures a fluid-tight seal due to the small size of the aperture formed in the diaphragm by the needle.

In spite of the advantages associated with needle type injection sites, there is a recognized need for replacing such an injection site with one which eliminates the needle in order to avoid the disadvantages associated therewith including the possibility of medical personnel receiving a puncture wound during the use thereof and the progressive deterioration of the diaphragm resulting from repetitive puncturing of the diaphragm.

One proposed solution for eliminating needles at coupling sites includes providing a valve member having a slit for receiving a blunt cannula therethrough wherein the slit is biased to a closed position such that a fluid-tight seal is formed at the valve member when the cannula is removed.

U.S. Pat. No. 4,765,588 to Atkinson discloses a valve for receiving the blunt end of a syringe and includes a slit diaphragm member mounted within a tubular body wherein the diaphragm is stretched in the area of the slit and moves in close to the tubular body as a luer taper portion of the syringe is inserted. In addition, the exterior wall of the body portion is dimensioned to be received within a threaded locking collar of the syringe surrounding the luer taper whereby an additional fluid-tight seal is formed with the valve.

It has been recognized that it is not only desirable to provide a valve adapted to receive a blunt cannula such as the luer taper of a syringe, as is disclosed by the above Atkinson patent, it is also desirable to provide a connection or coupling which positively locks the blunt cannula to the coupling site and thereby prevents inadvertent removal of the cannula during use. A concept for providing a mechanical lock between a blunt cannula and an injection site is disclosed in PCT Publication No. WO 90/11103 which discloses an injection site having a housing mounting a preslit septum and means for mechanically coupling a specially adapted cannula to the housing. One such special cannula contemplates providing a female luer connection for threadably engaging within the threaded locking collar of a male luer lock fitting on a syringe and further includes a specially configured blunt cannula having a tapered end for passing through the preslit septum of the valve. In addition, the housing holding the septum may be provided with threads for engaging coupling threads located interiorly of a shield surrounding the cannula.

It should be noted that in the above-described site, the outer diameter of the housing is formed larger than the inner diameter of the threaded collar on the syringe in order to provide sufficient space for the septum which expands outwardly into an annular space during insertion of a cannula.

There is a need for a medical coupling site that is usable with blunt cannula such as are provided by standard male luer lock fittings having a male luer taper surrounded by a threaded locking collar and in which the site is provided with a valve element and means for directly engaging the threads on the locking collar to form a mechanical connection. It should be noted that such a site is highly desirable in that standard dimensions for both male and female luer taper fittings have been recognized by both the American National Standards Institute, Inc. (ANSI) and by the International Organization for Standardization (ISO). Thus, the fittings formed on the ends of syringes, as well as fittings for the majority fluid connections used in medical applications throughout the world, conform to the ANSI and ISO standards and a coupling site incorporating a valve for use with such standard fittings would provide the advantage of allowing a positive mechanical connection to be formed at the coupling site as well as eliminate the need for the use of needles or special cannula to penetrate the valve element, and thus would overcome disadvantages associated with prior art coupling sites.

Elimination of the need for a special cannula for use at the coupling site would also provide a cost advantage in that only the coupling site would need to be purchased and existing fittings could be used in conjunction with this site.

One problem associated with providing a coupling site for use with a standard male luer lock results from the limited space provided between the outer surface of the male luer taper and the inner surface of the threaded locking collar which makes it difficult to provide both a rigid locking surface on the outside of the fitting for engaging the locking collar and a flexible valve element of sufficient size and resilience to releasably accommodate the male luer taper.

Thus, the Atkinson patent described above describes a valve element which may be used with a luer fitting, but in which the outer surface of the elastomeric valve element is received in contact with the locking collar without the inclusion of any rigid member for engaging the threads within the collar. The PCT publication described above discloses an alternative approach to the same problem in that the adapter provided for attachment to a standard luer lock is provided with a locking collar which is larger than the locking collar provided on the male luer lock, thus permitting the coupling site to be constructed with an enlarged diameter to accommodate a sufficiently large septum for receiving a cannula having the desired diameter for providing sufficient flow through the site.

There are certain physical design limitations to providing a valve element which will both receive a luer taper as well as reliably reseal after the luer taper is removed. Several prior art valves for receiving a luer taper provide a thick disk or septum, such as is disclosed in the above-noted PCT publication, wherein the disk or septum is formed with a sufficient amount of resilient material around the slit to close the slit when a cannula is not present. Space must be provided in order to accommodate the distortion of material around the slit as the cannula is inserted and this space must either be provided within the fluid passage area for receiving the cannula or within the housing supporting the disk or septum, such as may be provided by an annular space directly adjacent to the outer periphery of the disk or septum.

Alternatively, the slit may be formed in a relatively thin diaphragm, such as is disclosed in the Atkinson patent, wherein sufficient space for receiving the distorted portions of the diaphragm around the slit is provided within a space defined by a tubular body portion for receiving the luer taper.

Thus, it is apparent that in any coupling site sufficient space must be provided around the circumference of any valve member in order to accommodate distortion of the resilient material forming the valve member such that little space is available for additionally accommodating a rigid member adapted to engage the threaded locking collars surrounding the male luer taper. Further, if the material surrounding the slit portion of the valve element is reduced, the forces provided by the material to resiliently bias the slit to a closed position are also reduced and thus may result in an undesirable structure which will not positively seal the slit closed upon removal of a cannula or luer taper.

It should further be noted that it is preferable to provide a coupling site which is adapted to receive cannula having a diameter at least as large as a standard male luer taper in order to avoid introducing any restriction to flow at the site with resulting reductions in the flow rate.

A further problem associated with prior art coupling sites relates to the ability of a male luer to easily slide across the surface of the diaphragm as it is inserted through the diaphragm. Typically, wiping of a valve site prior to insertion of a male luer therethrough causes the valve surface to become increasingly less slippery resulting in the male luer tending to stick to the surface of the valve element rather than sliding across the surface of the valve as it is inserted through the diaphragm.

Accordingly, there is a need for a medical fluid path coupling site which may be coupled directly to a standard male luer lock including means for forming a mechanical connection with a threaded locking collar portion of the luer lock. In addition, there is a need for such a site including a valve in which a slit for receiving a male luer taper portion of the male luer lock is positively biased to a closed position to prevent leakage through the valve when the male luer taper is removed.

Further, there is a need for a medical coupling site wherein the valve is provided with a surface for reducing friction between a male luer and the valve whereby insertion of a male luer through the valve is facilitated.

SUMMARY OF THE INVENTION

The present invention provides a coupling site for use in medical fluid flow applications wherein the coupling site is adapted for use with a standard male luer lock having a male luer taper and a threaded locking collar. The medical coupling site of the present invention is preferably configured for use with a male luer lock constructed according to ANSI and ISO standards such that the coupling site of the present invention is adapted for immediate use in fluid flow paths currently in use throughout the world without the necessity of any adapter couplings being provided between the coupling site and existing standard luer fittings.

The medical coupling site of the present invention includes a support base defining a longitudinal axis for the coupling site, and a retainer supported on the base. A valve element is located within the retainer and includes a substantially tubular body portion having first and second ends and a diaphragm member extending across the first end of the body portion.

Lug means are provided extending radially outwardly from the retainer for engaging threads on the threaded locking collar of the male luer lock. The lug means are preferably located at an end of the retainer adjacent to the diaphragm member of the valve element.

The body portion of the valve element includes an outer wall in contact with an inner wall of the retainer. In addition, an inner wall of the valve element body portion defines a tubular passage for receiving the male luer taper portion of the male luer lock.

The diaphragm member includes means defining a slit extending diametrically across the diaphragm member, and biasing means extend inwardly from the inner wall of the body portion toward the slit for biasing the slit to a closed position. The biasing means preferably include discrete members, such as ribs, extending radially inwardly in a direction from the second end of the body portion toward the first end thereof. The biasing means increase the effectiveness of the diaphragm to quickly close the slit when a cannula or luer taper is not present while also providing space for the deformation of the diaphragm member during insertion of a cannula or luer taper.

Thus, while the diaphragm is formed as a highly flexible element permitting easy insertion of a cannula into the valve, the biasing means ensure that the slit is positively sealed when a cannula is not present.

Further, in order to provide a coupling site structure which will fit between the male luer taper and threaded locking collar of a male luer lock, the retainer is formed as a thin structure relative to the body portion. In the preferred embodiment, a thickness of the body portion, as measured in a direction perpendicular to the longitudinal axis, is greater than a thickness of the retainer, measured in the same direction, at a location adjacent to the lug means. Further, the retainer is preferably formed from thin metal and the lug means are formed as first and second protrusions formed in the metal on opposite sides of the retainer.

The retainer extends from a location adjacent to the first end of the body portion to a location adjacent to the support base and the body portion of the valve element extends along the retainer and is positioned in contact with the support base such that fluids flowing through the coupling site will not contact the retainer. The body portion is preferably sandwiched between the retainer and the support base at the second end of the body portion whereby the valve element is held in place relative to the support base.

In one embodiment of the coupling site, the diaphragm of the valve element is formed having a concave outer surface and a convex inner surface wherein the concave surface has a peripheral edge located closely adjacent to an annular end surface of the body portion. Further, the concave surface is relatively shallow such that it may be easily sterilized prior to insertion of a cannula.

In a further embodiment of the coupling site, the diaphragm of the valve element is formed having a substantially planar outer surface. The outer surface is formed having a predetermined rough surface texturing whereby the frictional forces between a male luer and the diaphragm are decreased. In addition, the rough surface texturing defines a plurality of hills and valleys wherein a lubricous substance may be located and retained within the valleys during wiping of the exposed surface with a sterile wipe. Thus, the surface texturing facilitates retention of the lubricous substance for lubricating insertion of a male luer through the diaphragm.

Therefore, it is an object of the present invention to provide a medical coupling site which provides a secure connection with a standard male luer lock, such that medical personnel receive a positive feedback of a locked connection when the device is in use.

It is another object of the present invention to provide a coupling site which ensures a secure seal to a medical fluid flow line both when a cannula is present at the site and when a cannula is absent.

It is a further object of the present invention to provide a medical coupling site which provides a minimal resistance to insertion of a cannula.

It is yet another object of the present invention to provide a medical coupling site which is economical to produce, which has a simple design and which requires minimal usage instructions such that the site may be readily placed in use without disruption to systems currently in place.

Other objects and advantages of the invention will be apparent from the following description, the accompanying drawings, and the appended claims.

BRIEF DESCRIPTION OF THE DRAWINGS

FIG. 3 is a view similar to FIG. 2 in which the male luer lock fitting is shown inserted into the coupling site prior to threaded engagement of the male luer lock fitting with the coupling site;

FIG. 4 is a cross-sectional view of the coupling site taken along line 4—4 in FIG. 1;

FIG. 5 is a cross-sectional view taken along line 5—5 in FIG. 2;

FIG. 6 is a perspective view of a second embodiment of the medical coupling device of the present invention;

FIG. 7 is a cross-sectional view taken along line 7—7 in FIG. 6, and additionally showing a male luer lock fitting for connection to the coupling site;

FIG. 8 is a cross-sectional view similar to FIG. 7 in which the male luer lock fitting is shown inserted into the coupling site prior to threaded engagement of the male luer lock with the coupling site;

DETAILED DESCRIPTION OF THE PREFERRED EMBODIMENT

Figure 1:
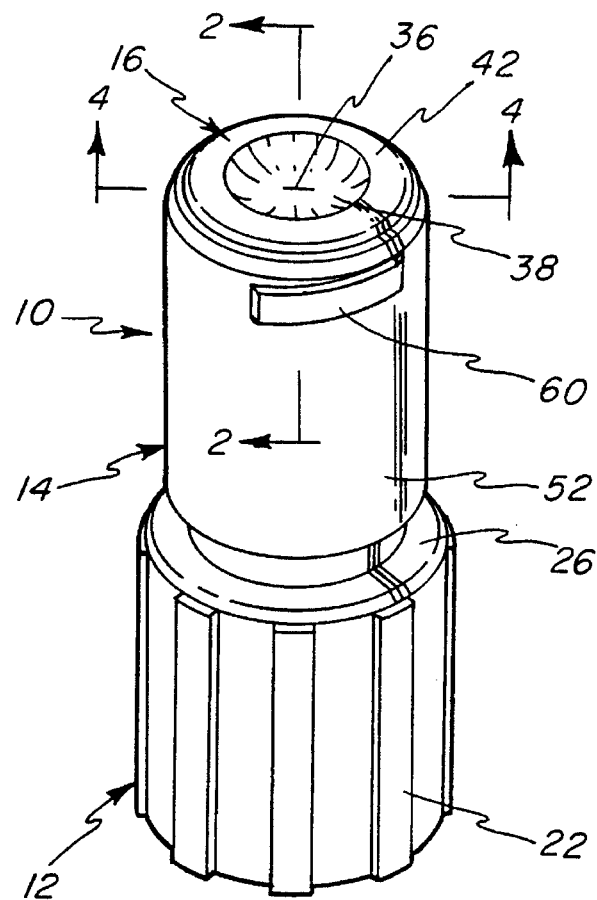
FIG. 1 is a perspective view of the medical coupling site of the present invention.

Referring to FIGS. 1–5, a first embodiment of the medical coupling site is shown and is designated generally by reference numeral 10. As may be best seen in FIGS. 1, 2 and 4, the coupling site 10 generally includes a support base 12, a retainer 14 supported on the support base and a valve element 16 located within the retainer.

In the preferred embodiment, the support base 12 is formed from a plastic material, the retainer 14 is formed from a metal material such as coated aluminum, and the valve element 16 is formed of an elastomeric material such as an elastomer which conforms to standard medical specifications. However, it should be noted that other materials may be used for forming the particular elements of the present medical coupling site 10 to the extent that the alternative materials permit the coupling site 10 to function with the advantages to be described below.

Figure 2:
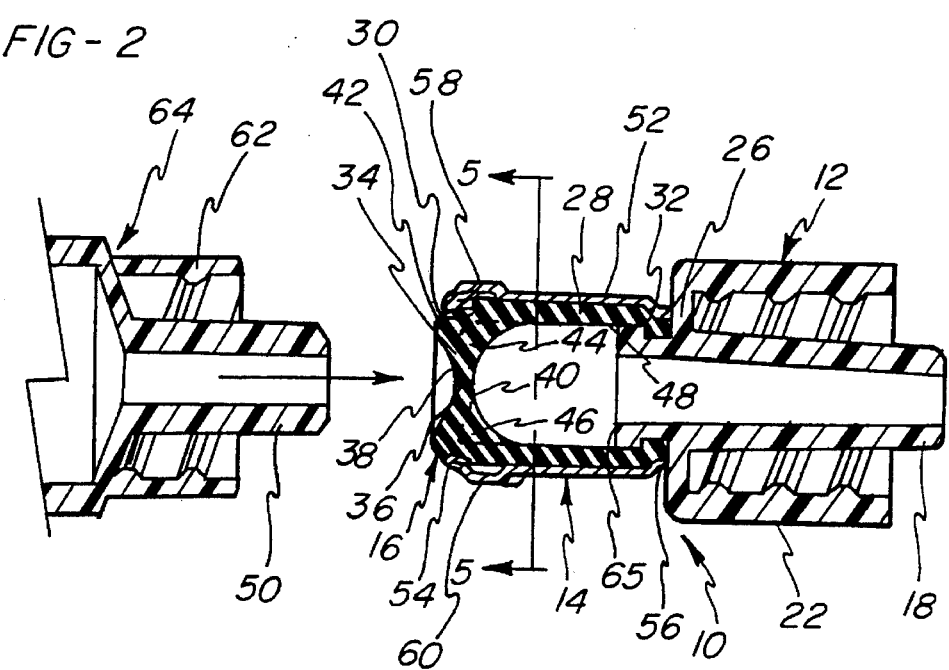
FIG. 2 is a cross-sectional view of the coupling site taken along line 2—2 in FIG. 1, and additionally showing a male luer lock fitting for connection to the coupling site.

As seen in FIGS. 2 and 4, the support base 12 preferably includes a tubular luer taper portion 18 defining a longitudinal axis 20 of the coupling site 10. The luer taper portion 18 is surrounded by a threaded locking collar 22 such that the coupling site 10 may be attached to a standard female luer fitting. In addition, an outwardly extending flange portion 24 is attached to an inner end of the luer taper portion 18 extending from an end wall 26 of the collar 22.

The valve member 16 includes a tubular body portion 28 extending substantially parallel to the longitudinal axis 20 and defining a first end 30 and a second end 32 wherein the second end 32 is in contact with the support base 12 adjacent to the end wall 26. The valve element 16 further includes a thin flexible diaphragm 34 extending across the first end 30 of the body portion 16.

The diaphragm 34 includes means defining a slit 36 extending diametrically across the diaphragm 34. In addition, the diaphragm 34 defines opposing first and second sides 38, 40 wherein the first side 38 is formed as a concave surface and the second side 40 is formed as a convex surface. The concave first surface 38 includes a peripheral edge lying in a plane defined by an annular end surface 42 of the body portion 16.

It should be noted that the first surface 38 is provided with a relatively shallow curvature such that the first surface 38 is easily cleaned by wiping of the surface. Also, as a result of forming the diaphragm 34 curved inwardly toward the port base 12, fluid pressure within the site 10 will exert an outwardly directed force on the diaphragm 34 and will tend to cause the material surrounding the slit 36 to compress inwardly, thus biasing the slit closed.

Further, although the second surface 40 is shown having a substantially cylindrical curvature, it should be noted that this surface may also be formed having a spherical or dome-shaped curvature.

Referring to FIGS. 2, 4 and 5, the valve element 16 is further provided with biasing means which are preferably in the form of first and second ribs 44, 46 extending radially inwardly from an inner wall 48 of the body portion 16 toward the slit 36 in a direction from the second end 32 toward the first end 30. As may be best seen in FIG. 5, the rib members 44, 46 are oriented such that they intersect and extend parallel to a plane which intersects the longitudinal axis 20 and extends perpendicular to the slit 36. In addition, each of the rib members 44, 46 define a width dimension in a direction parallel to the slit 36 which is less than an interior diameter defined by the inner wall 48 of the valve body 16. Thus, the rib members 44, 46 have a dimension in a direction parallel to the longitudinal axis 20 which decreases in a direction from the inner wall 48 toward the slit 36.

The rib members 44, 46 reinforce the diaphragm 34 and act to bias the slit 36 to a closed position. Further, by providing rib members 44, 46 which have a width dimension less than the inner diameter of the body portion 16, the space surrounding the rib members 44, 46 is available to accommodate elastomeric material of the diaphragm 34 and body portion 28 as the valve element 16 is distorted during insertion of a male luer taper 50 (see FIG. 2).

Referring to FIGS. 1, 2 and 5, the retainer 14 is formed as a tubular sleeve defined by an elongated body 52 having a first end 54 adjacent to the first end 30 of the valve element 16 and a second end 56 adjacent to the second end 32 of the valve element 16.

The first end 54 of the retainer 14 is turned inwardly into the first end of the valve element 16 and is preferably folded over to form a double thickness portion. This portion forms a reduced area for slightly compressing the valve element 16 in the area around the diaphragm 34 to thereby form a seal preventing fluids from passing between the valve element 16 and the retainer 14.

The second end 56 is preferably crimped inwardly toward a gap formed between the flange portion 24 and the end wall 26 to thereby hold the second end 32 of the valve element 16 under the flange portion 24 such that the valve element 16 is firmly held in place on the support base 12. Thus, the valve body portion 28 extends substantially along the length of the retainer 14 and isolates the retainer 14 from fluids flowing through the coupling site, as well as forms a direct fluid path through the site 10 to avoid the formation of crevices or pockets which may retain fluids and hinder flushing of the site between administration of different medicines.

In addition, the inner surface of the elongated body 52 preferably defines a diameter which is slightly smaller than the outer diameter of the body portion 28 prior to mounting in the coupling site 10. Thus, the retainer 14 firmly engages the valve element 16 and applies a predetermined compression force for further biasing the material surrounding the slit 36 inwardly toward the axis 20 for closing the slit 36.

The retainer 14 further includes a pair of lugs 58, 60 extending radially outwardly from the outer surface of the retainer body 52. It should be noted that the retainer 14 is preferably formed from thin material such as coated aluminum, which may be conveniently stamped to a desired shape. Thus, the lugs 58, 60 may be formed as stamped protrusions in the body 52.

The lugs 58, 60 are configured to engage the double helix threads formed on the interior of a threaded locking collar 62 (see FIG. 2) for a standard male luer lock. Thus, the lugs 58, 60 may be formed extending at a slight angle relative to a plane extending perpendicular to the longitudinal axis 20. In addition, it should be noted that the lugs may be formed having an alternative configuration, such as a configuration defining threads extending around the entire circumference of the retainer body 52 and that other means of forming the thin metal retainer, such as machining, may be applied.

The lugs 58, 60 are preferably located adjacent to the first end 54 of the retainer 14 and the thickness of the retainer body portion 52 in at least the area adjacent to the lugs has a thickness, as measured in a direction perpendicular to the longitudinal axis 20, which is less than the thickness of the valve element body portion 28. The relationship between the thickness of the retainer 14 and the valve element 16 is important since only a limited amount of space is available between a standard male luer taper 50 and the surrounded locking collar 62. Thus, in the configuration of the present invention, it is desirable to provide a maximum amount of material for the resilient valve element 16 in order to form a positive seal while providing a retainer 14 of minimal thickness to form the locking connection with the threaded locking collar 62.

It should particularly be noted that the present medical coupling site 10 is specifically designed for cooperation with a standard male luer lock having standardized dimensions, as specified by ANSI and ISO. Referring to FIG. 2, a standard male luer lock 64 is illustrated and may be in the form of a standard syringe end including a male luer taper 50 and a threaded locking collar 62. In accordance with ANSI and ISO standards, the male luer taper 50 has an outer diameter of approximately 3.9 mm to 4.0 mm and the threaded locking collar 62 has a minimum inner diameter, as defined by the threaded portion of approximately 7.0 mm to 7.2 mm. In addition, the male luer taper is formed tapering inwardly at an angle of 6°. Thus, the retainer 14 of the coupling site 10 is formed having a maximum outer diameter for the retainer body 52 of approximately 7.0 mm, and the inner wall 48 of the valve element 16 defines a minimum diameter of 4 mm.

As shown in FIG. 3, the configuration of the present coupling site 10 results in a site which is particularly adapted to be received between the male luer tip 50 and the locking collar 62 with the outer surface of the site 10 forming a positive mechanical connection with the threads of the collar 62 and with the interior of the valve body 28 providing sufficient clearance for the male luer taper 50 to easily slide into the coupling site 10. In addition, end surface 65 of the luer taper 18 may serve as a convenient stop surface for engaging the end of the luer taper 50 to define a positive lock position between the male luer lock 64 and the coupling site 10.

With reference to FIG. 3, it should also be noted that the male luer taper 50 causes the diaphragm 34 to be stretched and pushed into a distorted position adjacent to the inner wall 48, with an accompanying distortion of the ribs 44, 46.

Further, the coupling site 10 of the present invention incorporates a flexible diaphragm member 34 having a slit 36 wherein the slit is biased to a closed position through forces exerted on the diaphragm member by a supporting tubular body portion 28 forming a passage for receiving the male luer taper. Providing such a diaphragm member 34 for forming the seal on the site end results in a highly resilient opening offering reduced resistance to forces pushing the male luer taper 50 or other cannula into the coupling site 10 while also providing a reliable closure element when the male luer taper 50 is removed from the site 10.

In addition, the present coupling site 10 may also easily be used with a needle in that a needle may be inserted through the diaphragm 34 in the region surrounding the slit 36 if it should be necessary to infuse or withdraw fluids through a needle at the injection site.

Referring to FIGS. 6–8, a second embodiment of the present invention is shown and is designated generally as 10'. In addition, elements in the second embodiment corresponding to elements in the first embodiment are labeled with the same reference numeral primed. The embodiment of FIGS. 6–8 differs from the previous embodiment in that the area surrounded by the flange portion 24' includes an enlarged passage defining a luer slip 66' which is adapted to receive the end of a standard male luer taper 50'. The area of the second end 32' of the body portion 16' and the second end 56' of the retainer 14' are formed with an enlarged diameter, as compared to the previous embodiment, in order to accommodate the enlarged luer slip area 66'.

The portion of the valve body 28' and the retainer body 52' adjacent to the lugs 58', 60' is formed with the same diameter as in the previous embodiment such that the coupling site 10' will cooperate with a standard male luer lock 64' in the same manner as in the previous embodiment. However, it should be noted that as the luer taper 50' is inserted into the coupling site 10' and the locking collar 62' is threadably engaged with the retainer 14', the tip of the luer taper 50' will pass into the luer slip 66' whereby an additional seal is formed between the exterior of the luer taper 50' and the interior of the luer slip 66'. In addition, the contact between the luer taper 50' and luer slip 66' defines a positive lock position between the luer lock 64' and the coupling site 10'.

It should also be noted that the alternative configuration of FIGS. 6–8 does not affect the advantages afforded by passage of the retainer 14' and valve element 16' in between the luer taper 50' and the locking collar 62' to form a sealed connection wherein the standard luer lock 64' is mechanically locked onto the coupling site 10'.

Figure 9:
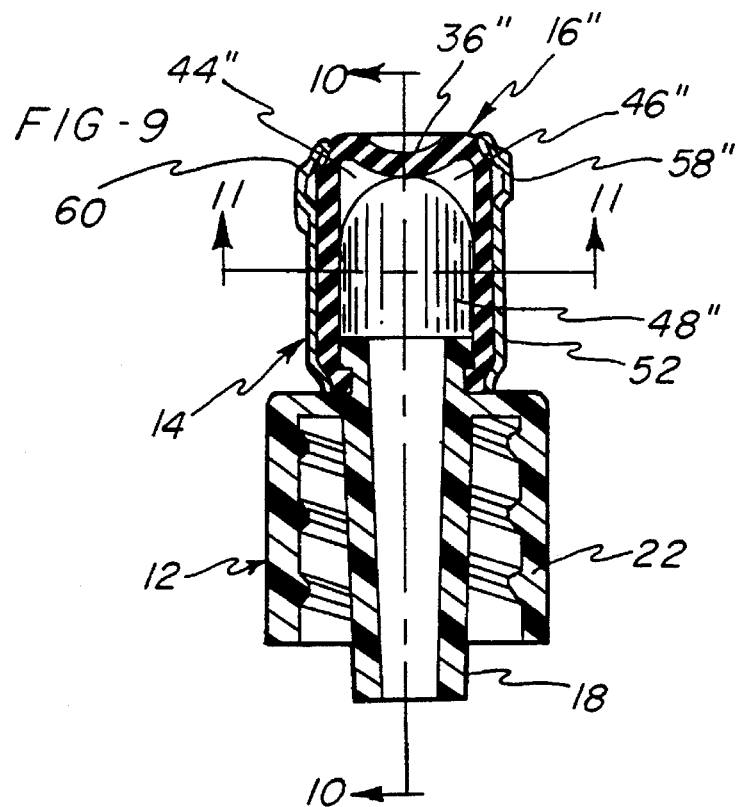
FIG. 9 is a cross-sectional view similar to that shown in FIG. 2 illustrating an alternative configuration for the valve element.
Figure 10:
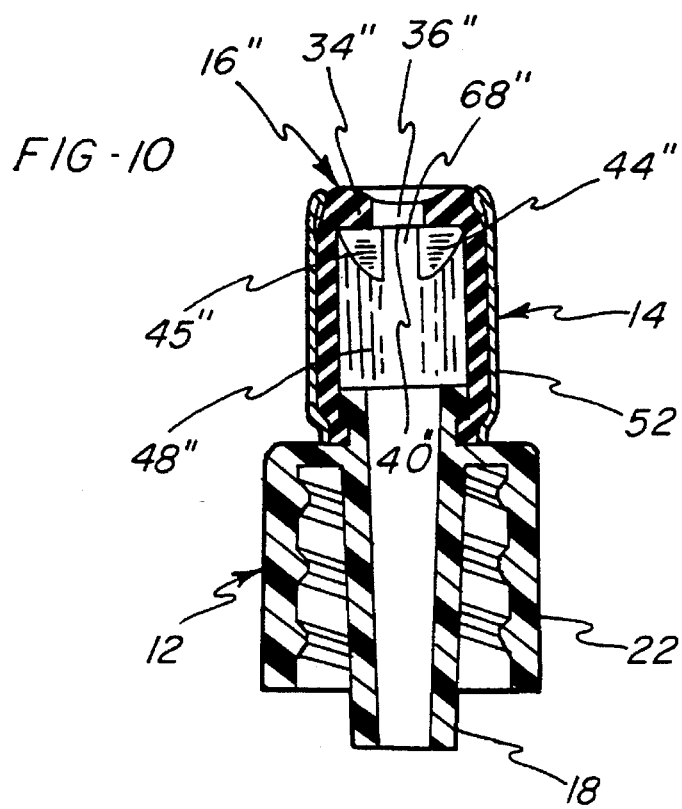
FIG. 10 is a cross-sectional view taken along line 10—10 in FIG. 9.
Figure 11:
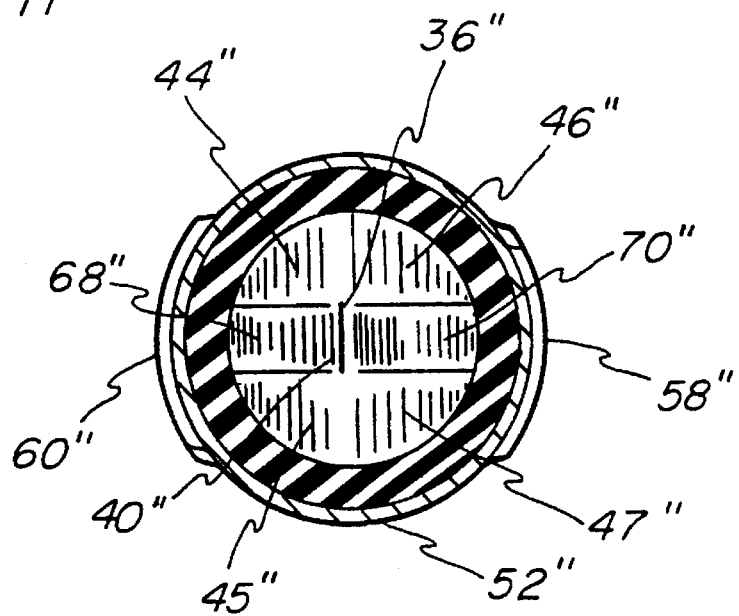
FIG. 11 is a cross-sectional view taken along line 11—11 in FIG. 9.

FIGS. 9–11 show an alternative to the first embodiment in which an alternative valve element 16" is shown and in which the elements for the retainer 14 and the support base 12 remain unchanged and are identified with the same reference numerals as in the first embodiment.

The valve element 16" of the present embodiment differs from the valve element 16 of the first embodiment in that a different rib structure is provided for biasing the slit 36" to a closed position. Specifically, a pair of rib portions 44", 45" and 46", 47" are provided on opposing sides of the slit 36". Each pair of rib members 44", 45" and 46", 47" is separated by a space 68", 70", respectively.

The rib members 44"–47" operate in the same manner as the ribs 44, 46 of the first embodiment to reinforce the diaphragm 34" and bias the slit 36" to a closed position In addition, the spaces 68", 70" provide an area for the material of the valve element 16" to deform into when a male luer taper is inserted into the coupling site.

It should be noted that other configurations for the rib members may be provided in order to bias the valve diaphragm to a closed position. For example, the curved surface of the ribs 44, 46 extending from the inner wall 48 of the valve element 16 to the slit 36 may be formed as a straight inwardly angled surface or may be provided with some other shape. In addition, it should be noted that the design of the diaphragm 34 and the reinforcing rib members 44, 46 for biasing the slit to a closed position may be altered to provide a predetermined resistance to back flow through the valve element 16. Thus, if it is desired for the coupling site 10 to provide a pressure relief function, such as when the coupling site 10 is used in a conventional Y-site with fluid being pumped into the Y-site through another opening, the valve element 16 may be designed to release fluid from the slit 36 at a predetermined pressure in order to avoid excessive pressure from being applied into a patient at an infusion site.

Finally, it should be noted that the diaphragm 34 may be formed as a planar element having opposing first and second sides which are substantially flat. By providing an outwardly facing planar surface, the valve of the present invention would be particularly easy to clean by wiping of the surface.

Figure 12:
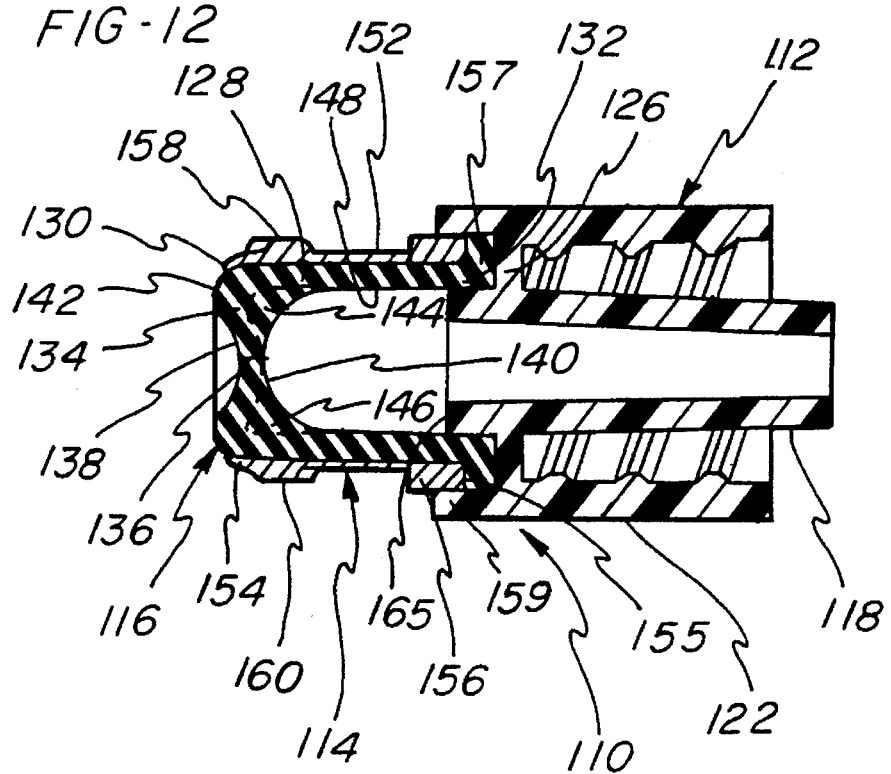
FIG. 12 is a cross-sectional view similar to that shown in FIG. 2 illustrating a further embodiment of the present invention.
Figure 13:
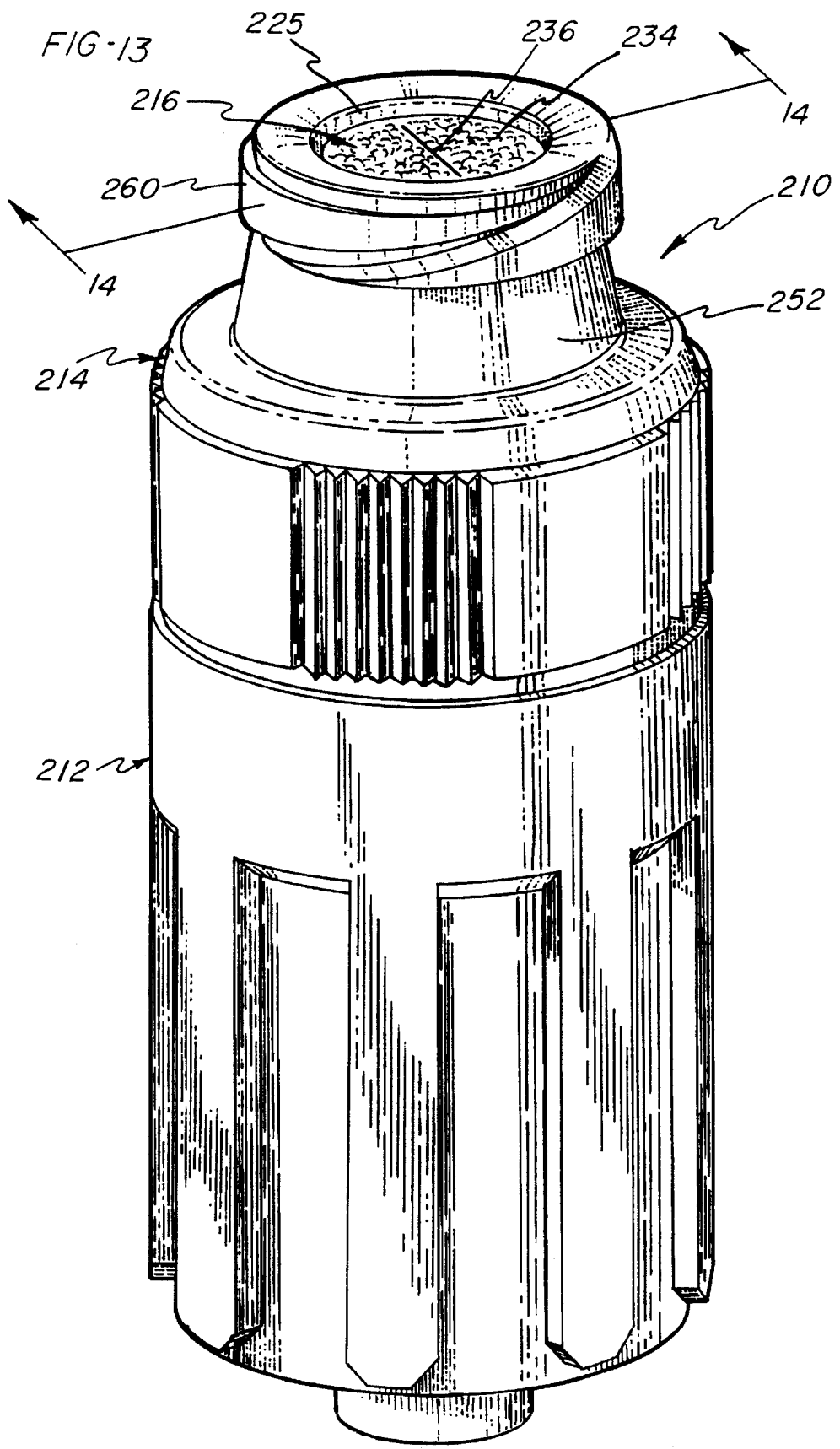
FIG. 13 is a perspective view of a further embodiment of the medical coupling device of the present invention.

FIG. 12 shows a further alternative embodiment to the first embodiment in which elements of the further embodiment corresponding to elements in the first embodiment are labeled with the same reference numerals increased by 100. In this embodiment, the retainer 114 is a formed thin element of any relatively rigid material such as metal or plastic. The second end 156 of the retainer includes an enlarged end surface 155 engaging a flange portion 157 of the valve element 116. The flange portion 157 is located within a groove defined between an inner end of the luer taper portion 118 and a lip 159 extending from the support base 112. The lip 159 firmly engages the enlarged second end 156 of the retainer 114 in frictional contact to positively maintain the elements of the coupling site 110 in position relative to each other. The coupling site 110 operates in a manner identical to that of the previous embodiments and differs only in the manner of forming the retainer 114 and in the structure for mounting the retainer 114 and the valve element 116 to the support base 112.

It should be noted that the retainer of the above-described embodiments may also be formed from a plastic material provided the plastic has sufficient rigidity to resist deformation during assembly and use of the coupling site.

FIGS. 13–19 illustrate yet another embodiment of the present invention.

Referring initially to FIGS. 13–19, the medical coupling site 210 of the present embodiment includes a base 212 supporting a rigid tubular retainer or housing 214, which is preferably formed of a plastic material. In addition, an elastomeric valve element 216 extends within the housing 214.

Figure 16:
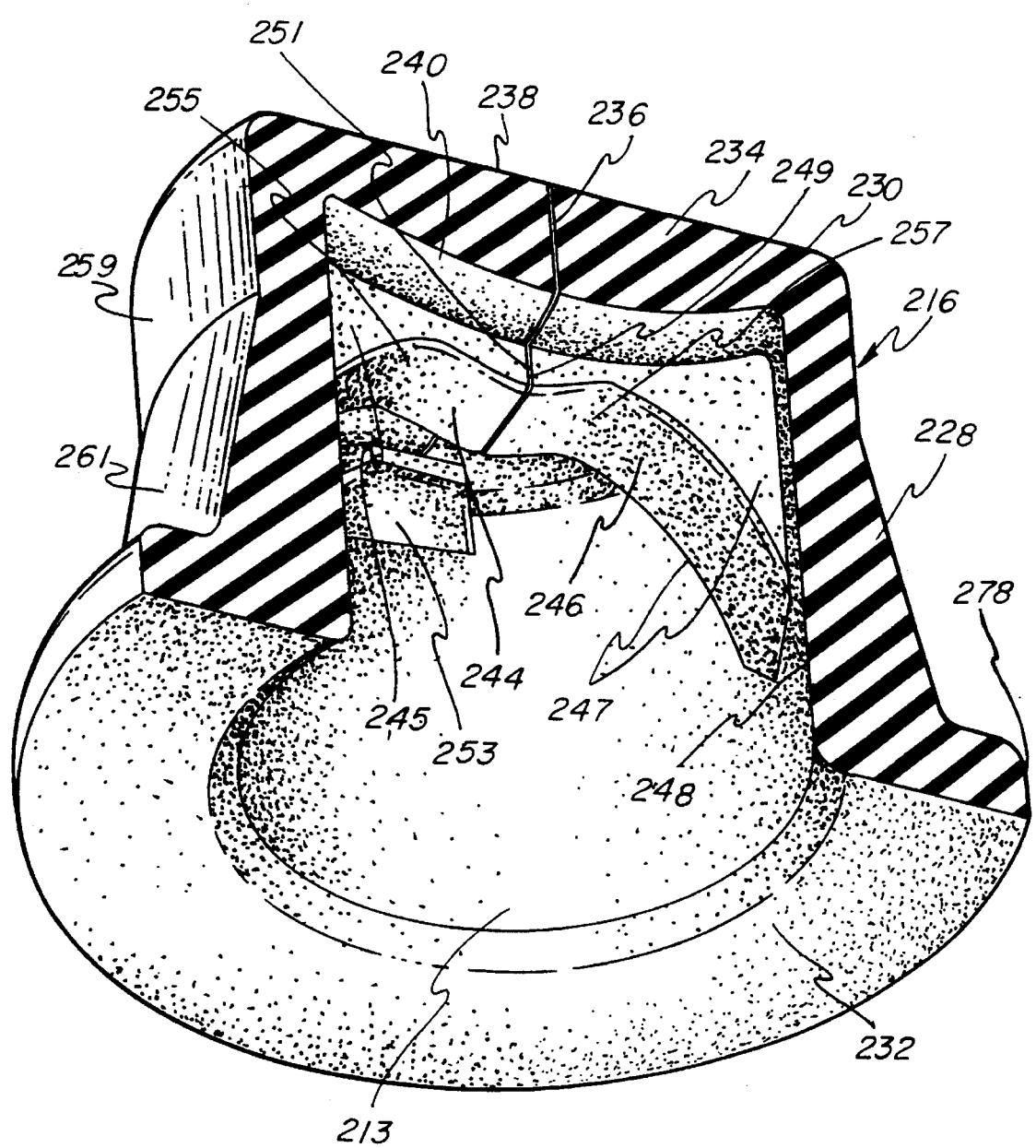
FIG. 16 is a partially cutaway bottom perspective view of the valve element used in the embodiment of FIG. 13.

Referring further to FIG. 16, the elastomeric valve element 216 includes a tubular body portion 228 and a diaphragm 234 formed integrally with the valve body 228 and extending across a first end 230 of the valve element 216. The diaphragm 234 includes a substantially planar exposed surface 238 and a convexly curved inner surface 240 which intersects a cylindrical inner wall 248 of the valve body 228 at an acute angle. The cylindrical inner wall 248 of the valve body 228 defines a luer receiving cavity 213 between the diaphragm 234 and a second end 232 of the valve element 216, and the inner surface 240 of the diaphragm 234 faces toward the luer receiving cavity 213.

The diaphragm 234 includes a slit 236 extending diametrically across and defining an opening through the diaphragm 234. A pair of biasing ribs 244, 246 extend radially inwardly toward each other from the cylindrical inner wall 248 to the inner surface 240 of the diaphragm 234. The rib 244 is defined by opposing, substantially planar side walls 245, and the rib 246 is defined by opposing, substantially planar side walls 247. The side walls 245, 247 extend into the luer receiving cavity 213 substantially perpendicularly from the inner surface 240 of the diaphragm 234. Each of the ribs 244, 246 further includes a respective facing surface 249, 251 extending substantially perpendicularly from the inner surface 240 of the diaphragm 234. The facing surfaces 249, 251 are located in alignment with the slit 236 and are in facing relationship for engagement with each other.

In addition, a pair of reinforcing ribs 253 (only one shown) are provided at opposing ends of the slit 236 and formed integrally with the diaphragm 234 and inner wall 248. The reinforcing ribs 253 prevent the diaphragm 234 from tearing at the ends of the slit 236 when a male luer is inserted through the diaphragm 234.

Each of the biasing ribs 244, 246 is formed with a respective hinge point 255, 257. The ribs 244, 246 are formed with thickened ends adjacent to the inner wall 248 and at the facing surfaces 249, 251, and the hinge points 255, 257 are defined by thin portions of the ribs 244, 246 intermediate the thickened ends. The hinge points 255, 257 facilitate flexing of the ribs 244, 246 when a male luer 288 (see FIG. 17) is inserted through the diaphragm 234. Further, the thickened portions adjacent to the facing surfaces 249, 251 facilitate preventing the diaphragm 234 from being pushed open by a fluid pressure from within the luer receiving cavity 213 in that the facing surfaces 249, 251 are adapted to engage each other to prevent outward flexing of the diaphragm 234 at the slit 236.

As seen in FIG. 16, the valve body 228 also includes a substantially cylindrical outer wall portion 259 adjacent to the first end 230 and an outwardly tapered outer wall portion 261 extending from a junction with the cylindrical outer wall portion 259 toward the second end 232 whereby a thickness of the valve body 228 progressively increases in a direction away from the first valve element end 230. A flange 278 extends radially outwardly from the outwardly tapered outer wall portion 261 at the second end 232.

Figure 14:
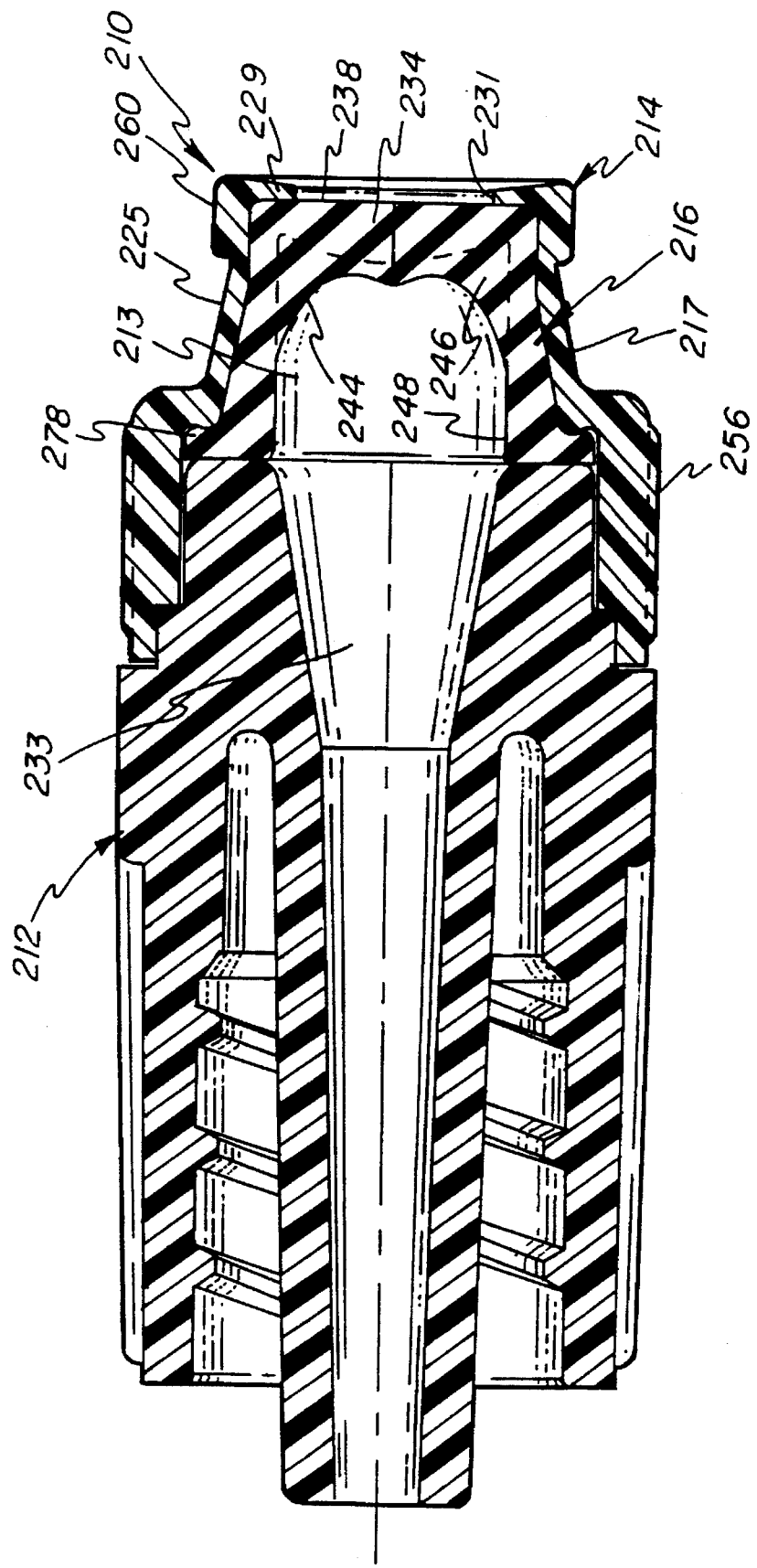
FIG. 14 is a cross-sectional view taken along line 14—14 in FIG. 13.
Figure 15:
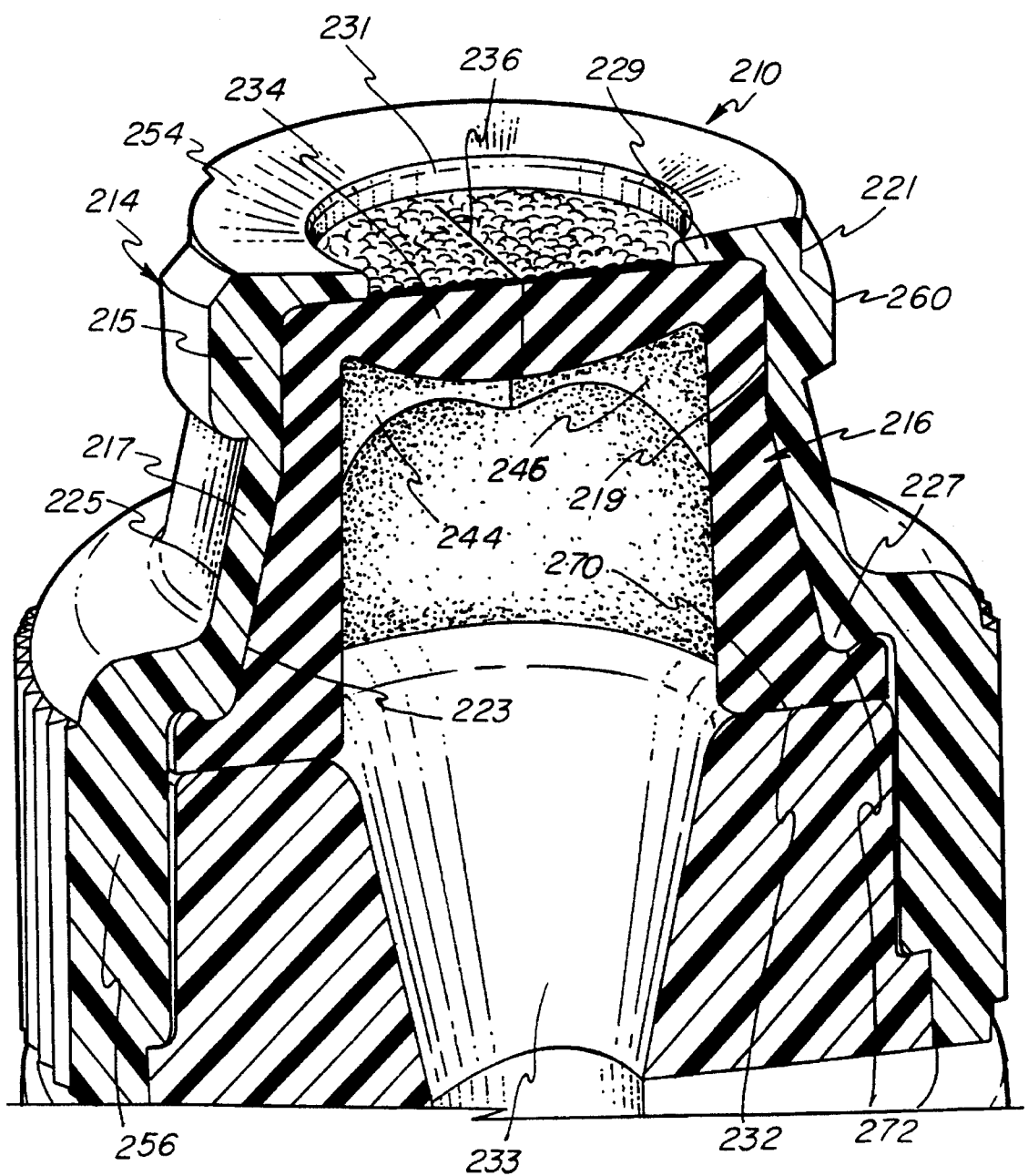
FIG. 15 is a perspective partially cutaway view of the embodiment of FIG. 13.

Referring to FIGS. 14 and 15, the housing 214 includes a substantially cylindrical portion 215 adjacent to a first end 254 of the housing 214, and an outwardly tapered portion 217 adjacent to the cylindrical portion 215 and extending toward a second end 256 of the housing 214. The cylindrical portion 215 includes cylindrical inner and outer walls 219 and 221 wherein the inner wall 219 substantially matches the configuration of the outer wall portion 259 of the valve element 216. The outwardly tapered portion 217 includes outwardly tapered inner and outer walls 223 and 225 wherein the inner wall 223 substantially corresponds to the configuration of the outer wall portion 261 of the valve element 216.

A double helix thread 260 is formed on the cylindrical outer wall 221 for engaging a threaded locking collar of a standard luer lock. Further, the outwardly tapered outer wall 225 tapers outwardly to a diameter greater than the interior diameter of a standard luer lock collar such that the luer lock collar may be frictionally locked into engagement with the coupling site 210 as the collar is threaded onto the thread 260. Further, the base 212 includes an opening 233 sufficiently large to permit free passage of the male luer taper into the base 212.

The second end 232 of the valve element 216 is adapted to rest on a surface 270 of the base 212. The thickened portion of the valve element 216 resulting from providing the outwardly tapered outer wall 261 provides the valve element 216 with increased column strength to help avoid buckling of the valve body 216 during insertion of a male luer into the luer receiving cavity 213. During insertion of a male luer, the forces exerted on the valve element will be directed radially outwardly against the outwardly tapered portion 217 of the housing 210 to thereby ensure that the valve element 216 maintains its shape and position within the housing 210.

Figure 17:
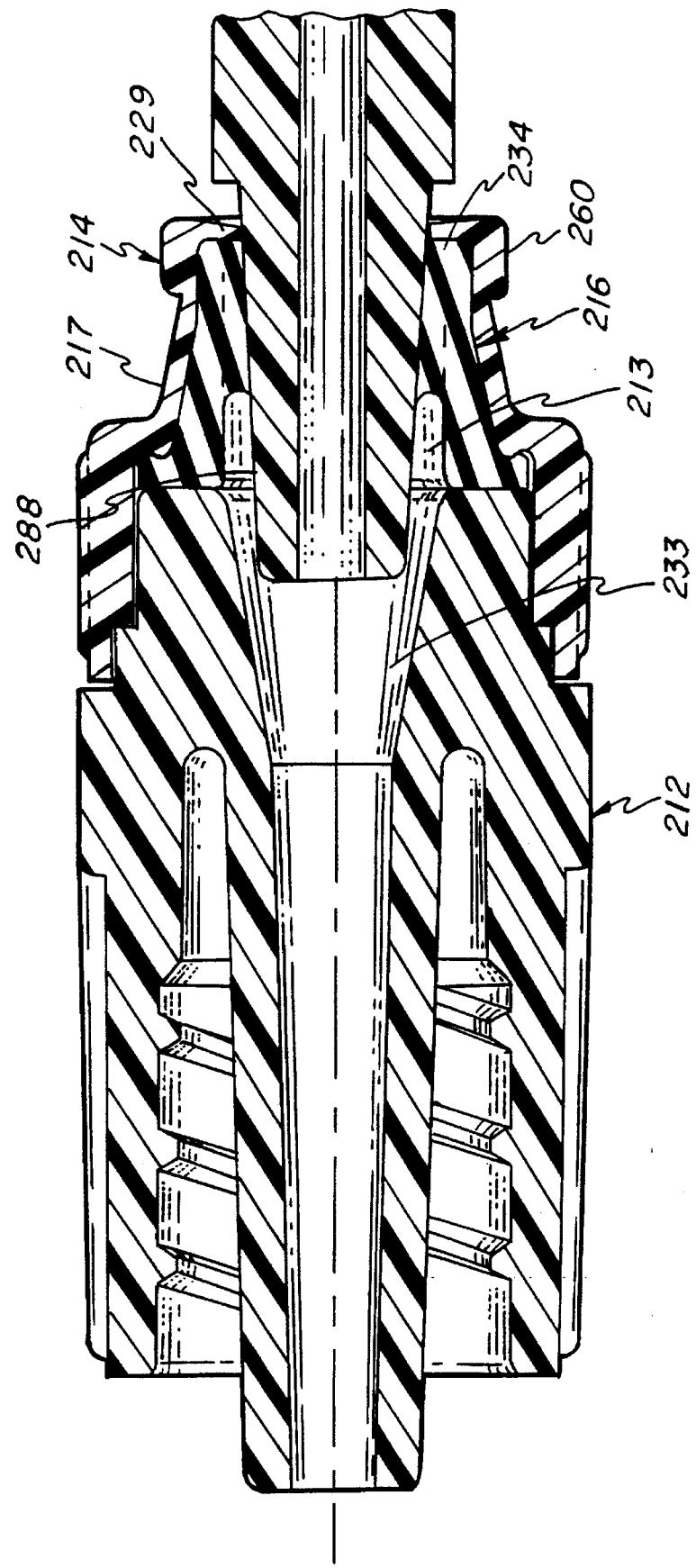
FIG. 17 is a cross-sectional elevational view showing a male luer slip inserted into the coupling site of FIG. 13.

The housing 210 is further provided with a locking flange 229 which extends radially inwardly at the first end 254. The flange 229 defines a locking edge 231 extending substantially perpendicular relative to the exposed surface 238 of the diaphragm 234. The edge 231 defines a diameter which is less than a diameter defined by the inner wall 248 of the valve element 216. The locking edge 231 is adapted to contact a male luer 288 in locking frictional engagement, as seen in FIG. 17. In other words, the diameter of the locking edge 231 is greater than the minimum diameter and less than the maximum diameter of a standard male luer taper 288, as defined by the ANSI and ISO standards, such that the present coupling site may be engaged in locking frictional engagement with a male luer taper 288 which does not have a threaded locking collar, as is illustrated in FIG. 17.

It should be noted that as a result of the flange 229 extending over the diaphragm 234 to a location radially inwardly from the radial location of the inner wall 248 of the valve element 216, the flange 229 also provides an additional biasing force on the upper portion of the diaphragm 234 for maintaining the slit 236 closed during high back pressure forces.

Figure 18:
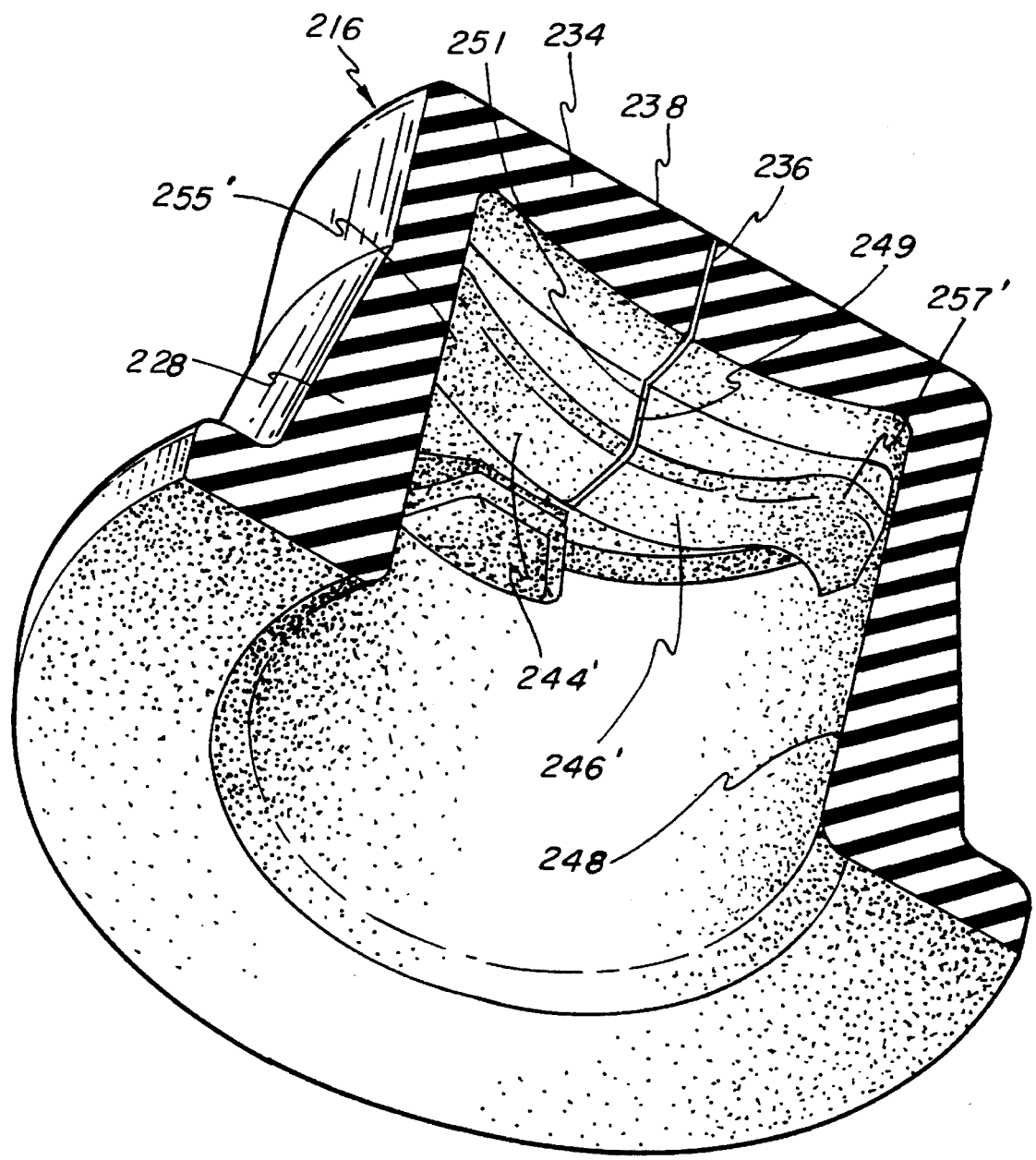
FIG. 18 is an alternative configuration for the valve element of the embodiment of FIG. 13.

Referring to FIG. 18, an alternative configuration for the valve element 216 of the present embodiment is illustrated. In this configuration of the valve element 216, the ribs, identified as 244' and 246', define a slightly different structure and the remainder of the valve element 216 is identical to the configuration previously described wherein identical elements are identified with the same reference numeral.

The ribs 244' and 246' differ from the previous configuration in that the location of the hinge points 255' and 257' are displaced closer to the inner wall 248 of the valve element 216. The different location for the hinge points 255', 257' provides different flexure characteristics for the diaphragm 234. Further, it should be noted that hinge points may be selected at additional points intermediate the locations shown in FIGS. 16 and 18.

Figure 19:
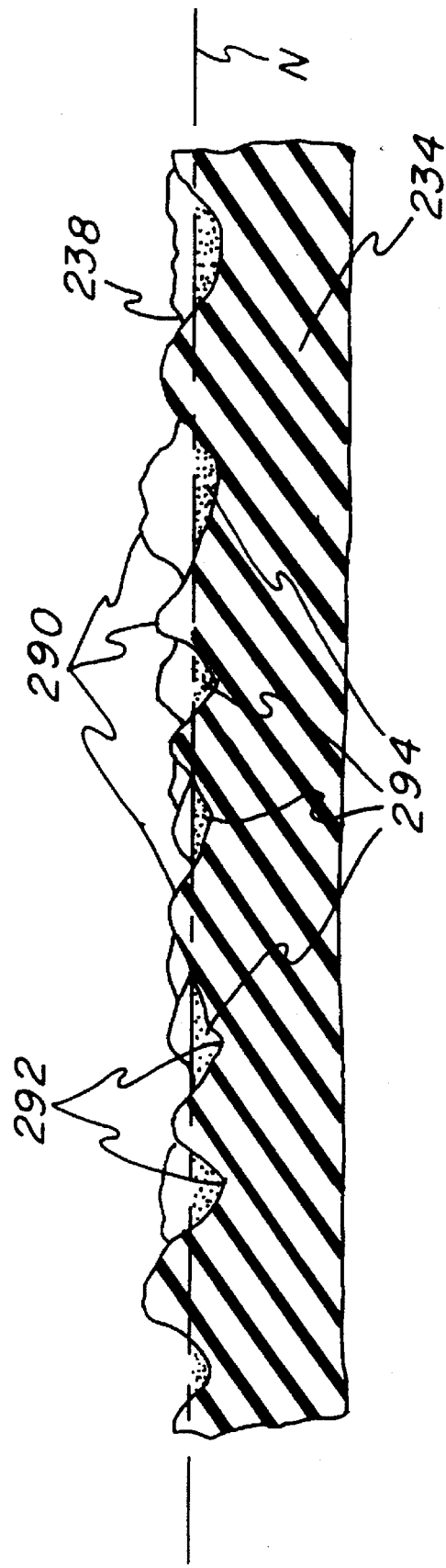
FIG. 19 is an enlarged cross-sectional view of an upper portion of the diaphragm in elevation illustrating the profile of the surface texture for the exposed surface of the diaphragm.

Referring to FIG. 19, the exposed surface 238 of the diaphragm is provided with a surface texturing which is rougher than that typically found on valve surfaces. The exposed surface 238 has a controlled roughness in order to facilitate insertion of a male luer taper through the diaphragm 234. Prior art valves having a diaphragm were typically produced having a roughness height value of 16 microinches, measured using the American standard ASA B46.1-1962. However, it has been found that the surface friction produced between a male luer and such a surface is undesirably high.

Accordingly, the exposed surface 238 of the present invention is formed having a American standard ASA roughness height value of approximately 180 microinches, and having a multi-directional lay. Thus, as seen in FIG. 19, the exposed surface 238 is formed with a plurality of minute hills 290 and valleys 292 extending above and below a nominal profile N of the exposed surface 238. By providing a surface having an increased roughness, the contact area between the diaphragm surface 238 and a male luer will be reduced since the male luer will contact only the tops of the hills 290 forming the rough surface.

In addition, the exposed surface may be provided with a medically acceptable lubricating substance 294, such as a fluid silicone lubricant, which will remain in the valleys 292, below the nominal profile N of the exposed surface 238, during wiping of the surface by a sterile wipe. Thus, in addition to reducing the contact area, the roughened exposed surface 238 facilitates retaining the lubricating substance 294 on the surface 238 during wiping. Further, the roughened surface permits the lubricant 294 to be retained on the surface to act as a lubricating coating as a male luer engages and distorts the diaphragm 234 during insertion through the slit 236.

From the above description, it should be apparent that the medical coupling site of the present invention overcomes the disadvantages associated with prior art sites. In particular, the present medical coupling site is provided with a wall structure having a sufficiently thin dimension to pass within the space defined between a standard male luer taper and a locking collar for a standard male luer lock fitting. In addition, the outer surface of the coupling site is provided with threads for engaging the double helix threads of the threaded locking collar for a male luer lock whereby the coupling site is held in fixed mechanical engagement with the male luer lock.

The above-described advantages of the present invention are particularly important considerations for obtaining acceptance of the medical industry in that prior art sites either required an enlarged adapter in order to accommodate a site incorporating a threaded mechanical coupling, or the sites provided only a friction fit for maintaining the site in contact with a luer taper or other cannula.

The present invention also has an advantage over prior art sites requiring a reduced diameter cannula for insertion through a valve element in that the present invention permits a standard luer taper to be inserted through the valve into the coupling site and the interior diameter of the coupling site is at least as large as the interior diameter of a standard luer taper. Thus, the coupling site of the present invention does not impose any restrictions to flow resulting from reductions of diameter within the site.

A further advantage of the present invention results from providing biasing means in the form of ribs for controlling the location of the diaphragm and thereby maintaining the slit in a closed position. Thus, the diaphragm of the present invention does not require excessive forces directed inwardly toward the slit in order to maintain the slit in a closed position, and as a result thereof the ease of insertion of a luer taper into the valve is greatly enhanced.

It should also be noted that the use of a thin rigid retainer in combination with a tubular valve element having a diaphragm extending across an end thereof provides a critical dual function of both providing a mounting structure for the threads and also acting as a reinforcing structure to rigidly support the valve element and thereby ensure closure of the slit, as well as prevent inadvertent opening of the slit resulting from side forces applied to the coupling site at the location of the valve element.

Other advantages associated with the present invention include the simplicity with which the medical coupling site may be incorporated into existing medical fluid systems without change over of equipment or the use of adapters to incorporate non-standard fittings. Also, while the present invention is particularly adapted to be used with standard male luer locks, it may also be used with other cannula or may be accessed with a conventional steel needle. The coupling site further provides for a positive feedback of a locked connection such that medical personnel will be able to quickly connect male luer lock fittings to the site.

In addition, the resiliency of the valve element diaphragm enables the present coupling site to be used for multiple insertions and with extended indwell times while maintaining its capability to form a fluid-tight seal at the slit upon removal of a luer taper or cannula. The design of the coupling site with the valve element extending from a point adjacent to the first end of the sleeve to a point in contact with the support base further ensures that crevices for containing pockets of fluid are avoided such that flushing of the valve in between administration of medicines is facilitated.

While the forms of apparatus herein described constitute preferred embodiments of the invention, it is to be understood that the invention is not limited to these precise forms of apparatus, and that changes may be made therein without departing from the scope of invention, which is defined in the appended claims.

What is claimed is:

1. A medical coupling site for use with a male luer, said coupling site comprising:

an elastomeric valve element including a tubular valve body defining first and second valve element ends, and a diaphragm extending across said first valve element end;

said valve body including a cylindrical inner wall defining a luer receiving cavity between said diaphragm and said second valve element end for receiving a male luer inserted through said diaphragm; and said valve body further including an outer wall whereby a valve body wall thickness is defined between said inner and outer walls;

said outer wall defining an outwardly tapered portion tapered outwardly in a direction from said first valve element end toward said second valve element end whereby said valve body wall thickness progressively increases in said direction from said first valve element end toward said second valve element end.

2. The coupling site as recited in claim 1 wherein said outer wall includes a substantially cylindrical portion adjacent to said first valve element end and extending toward said second valve element end to a junction with said outwardly tapered portion.

3. The coupling site as recited in claim 1 including a tubular housing surrounding said valve element, said housing having an inner wall portion tapered outwardly and engaging said outwardly tapered portion of said valve element.

4. The coupling site as recited in claim 3 wherein said tubular housing includes an outer wall portion tapered outwardly for engaging an inner wall of a standard luer lock collar in locking frictional engagement.

5. The coupling site as recited in claim 3 including a base, and a flange extending radially outwardly from said valve element, said flange being retained between said housing and said base.

6. A medical coupling site for use with a male luer, said coupling site comprising:

an elastomeric valve element including a tubular, substantially cylindrical valve body defining a cavity for receiving a male luer said cavity including opposing ends defining first and second valve element ends, and a diaphragm extending across said first valve element end to close off said cavity at said first valve element end, said diaphragm including an inner surface extending across said cavity and an exterior, exposed surface on a side of said diaphragm opposite said inner surface;

an opening defined in said diaphragm for receiving a male luer therethrough, said opening having a first uncoupled position wherein said opening is closed for sealing said cavity when a male luer is uncoupled relative to said site, and a second coupled position wherein said opening is open for receiving a male luer through said diaphragm when the male luer is coupled to said site and wherein said male luer is located extending into said cavity in said second coupled position;

wherein said exposed surface faces away from said cavity and includes surface texturing defining a predetermined surface roughness on said exposed surface for decreasing frictional forces upon engagement of a male luer with said diaphragm to thereby facilitate passage of said male luer through said diaphragm into said cavity.

7. The coupling site as recited in claim 6 wherein said predetermined surface roughness comprises a roughness height value greater than approximately 16 microinches to thereby define said surface texturing.

8. The coupling site as recited in claim 7 wherein said roughness height value is on the order of 180 microinches.

9. The coupling site as recited in claim 6 wherein said exposed surface includes a plurality of hills and valleys to define said surface texturing.

10. The coupling site as recited in claim 9 including a lubricious substance located in said valleys wherein said hills prevent said lubricious substance from being removed from said exposed surface during wiping of said diaphragm.

11. The coupling site as recited in claim 9 wherein said hills define small contact areas displaced from a nominal surface defined by said exposed surface such that an area for contacting a male luer is less than an area defined by said nominal surface.

12. The coupling site as recited in claim 6 including a tubular housing containing said valve element.

13. The coupling site as recited in claim 12 wherein said tubular housing includes a flange extending radially inwardly toward said diaphragm over a portion of said first valve element end.

14. A medical coupling site for use with a male luer, said coupling site comprising:

an elastomeric valve element having first and second ends and defining a longitudinal axis extending between said first and second ends;

a cavity defined between said first and second ends for receiving an end of a male luer;

a closure extending across said cavity to close off said first end, said closure having an exposed surface lying in a plane substantially perpendicular to said longitudinal axis for engaging a male luer and an opening having a first uncoupled position wherein said opening is closed for sealing said cavity when a male luer is uncoupled relative to said site, and a second coupled position wherein said opening is open for receiving a male luer through said closure when the male luer is coupled to said site and wherein an end of the male luer is located extending into said cavity in said second coupled position; and said exposed surface including surface texturing defining a predetermined surface roughness on said exposed surface for decreasing frictional forces upon engagement of a male luer with said valve element.

15. The coupling site as recited in claim 14 wherein said exposed surface includes a plurality of hills and valleys to define said surface texturing.

16. The coupling site as recited in claim 15 including a lubricious substance located in said valleys wherein said hills prevent said lubricious substance from being removed from said exposed surface during wiping of said diaphragm.

17. The coupling site as recited in claim 15 wherein said hills define small contact areas displaced from a nominal surface defined by said exposed surface such that an area for contacting a male luer is less than an area defined by said nominal surface.

18. The coupling site as recited in claim 14 wherein an opening is defined in said closure at said first end for receiving a male luer therethrough.

19. The coupling site as recited in claim 18 including a tubular housing containing said valve element.

20. The coupling site as recited in claim 19 wherein said tubular housing includes a flange extending radially inwardly toward said opening over a portion of said first valve element end.

21. A medical coupling site for use with a male luer, said coupling site comprising:

an elastomeric valve element including a tubular valve body defining first and second valve element ends, and a diaphragm extending across said first valve element end;

said valve body including a substantially cylindrical inner wall defining a cavity between said diaphragm and said second valve element end for receiving an end of a male luer inserted through said diaphragm;

a tubular housing including a substantially cylindrical outer wall surrounding said valve element, said housing including an insertion end adjacent to said diaphragm; and a flange extending radially inwardly from said outer wall at said insertion end and extending across said first valve element end, said flange defining a locking edge located radially inwardly from said outer wall for contacting a radially outwardly facing surface of a male luer in locking frictional engagement as an end of the male luer is inserted through said diaphragm into said cavity.

22. The coupling site as recited in claim 21 wherein said inner wall defines an inner diameter for said valve body, and said locking edge defines a diameter less than said inner diameter.

23. The coupling site as recited in claim 22 wherein said diaphragm includes an inner surface and said inner surface intersects said cylindrical inner wall at an acute angle.

24. The coupling site as recited in claim 21 wherein said diaphragm includes an exposed surface facing away from said luer receiving cavity and said locking edge extends substantially perpendicular to said exposed surface.

25. The coupling site as recited in claim 21 wherein said valve body includes a cylindrical inner wall and said diaphragm includes an inner surface facing said luer receiving cavity, and including a pair of biasing ribs extending radially inwardly toward each other from said cylindrical inner wall to said inner surface of said diaphragm, each said rib including a hinge point facilitating flexing of said ribs during insertion of a male luer through said diaphragm.

26. The coupling site as recited in claim 25 wherein each said rib includes a thickened end adjacent a central portion of said diaphragm and a thickened end adjacent said cylindrical inner wall, said hinge point being defined by a thin portion intermediate said thickened ends.

27. A medical coupling site for use with a male luer, said coupling site comprising:

an elastomeric valve element including a tubular valve body defining a longitudinal axis and first and second valve element ends, and a diaphragm extending across said first valve element end;

said valve body including a cylindrical inner wall defining a luer receiving cavity between said diaphragm and said second valve element end for receiving a male luer inserted through said diaphragm;

said diaphragm including an inner surface facing said luer receiving cavity;

an opening defined in said diaphragm;

a pair of biasing ribs extending radially inwardly toward each other from said cylindrical inner wall to said inner surface of said diaphragm, each of said ribs including a first end at said inner wall and a second end at said opening in said diaphragm, said first ends of said ribs having a first thickness, measured in a longitudinal direction parallel to said longitudinal axis, and said second ends of said ribs having a second thickness, measured in said longitudinal direction; and wherein each of said ribs includes a hinge point defined by a thickness, measured in said longitudinal direction, less than said first and second thicknesses and located on each of said ribs intermediate said first and second ends of said ribs to facilitate flexing of said ribs during insertion of a male luer through said diaphragm.

28. The coupling site as recited in claim 27 wherein each of said ribs includes a thickened portion adjacent to said opening to resist movement of said diaphragm outwardly away from said luer receiving cavity.

29. The coupling site as recited in claim 28 wherein each said thickened portion progressively increases in thickness in a direction from said hinge point toward said opening in said diaphragm.

30. The coupling site as recited in claim 27 wherein each said rib progressively increases in thickness in a direction from said hinge point toward said cylindrical inner wall.

31. The coupling site as recited in claim 27 wherein each said rib includes a thickened end adjacent a central portion of said diaphragm and a thickened end adjacent said cylindrical inner wall, said hinge point being defined by a thin portion intermediate said thickened ends.

32. The coupling site as recited in claim 27 wherein each said rib is defined by a pair of opposing side walls extending substantially perpendicularly from said inner surface of said diaphragm.

33. The coupling site as recited in claim 27 wherein each said rib includes a facing surface extending substantially perpendicularly from said inner surface of said diaphragm, and said facing surfaces being located in facing relationship for engagement with each other.

34. The coupling site as recited in claim 33 wherein said ribs each include a pair of opposing side walls adjacent to respective facing surfaces of said ribs, said side walls extending substantially perpendicularly from said inner surface of said diaphragm.

* * * * *